US00PP34872P2

(12) United States Plant Patent
Valin

(10) Patent No.: US PP34,872 P2
(45) Date of Patent: Dec. 27, 2022

(54) ***HYDRANGEA* PLANT 'TMHY18-1'**

(50) Latin Name: ***Hydrangea macrophylla* x *angustipetala***
Varietal Denomination: 'TMHY18-1'

(71) Applicant: Charles Valin, Ipswich (GB)

(72) Inventor: Charles Valin, Ipswich (GB)

(73) Assignee: Branded Garden Products

( * ) Notice: Subject to any disclaimer, the term of this patent is extended or adjusted under 35 U.S.C. 154(b) by 0 days.

(21) Appl. No.: 17/851,925

(22) Filed: Jun. 28, 2022

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Annette H Para
(74) *Attorney, Agent, or Firm* — Cassandra Bright

(57) ABSTRACT

A new and distinct cultivar of *Hydrangea* plant named 'TMHY18-1' is disclosed, characterized by lace-cap inflorescences having flowers with large, deeply serrated pure white sepals. Flowers are distinctly honey scented. Plants are remontant and have an upright, controlled habit. Flowering occurs on both terminal and axillary nodes. The new variety is a *Hydrangea*, typically produced as an outdoor ornamental plant.

2 Drawing Sheets

Figure 1:
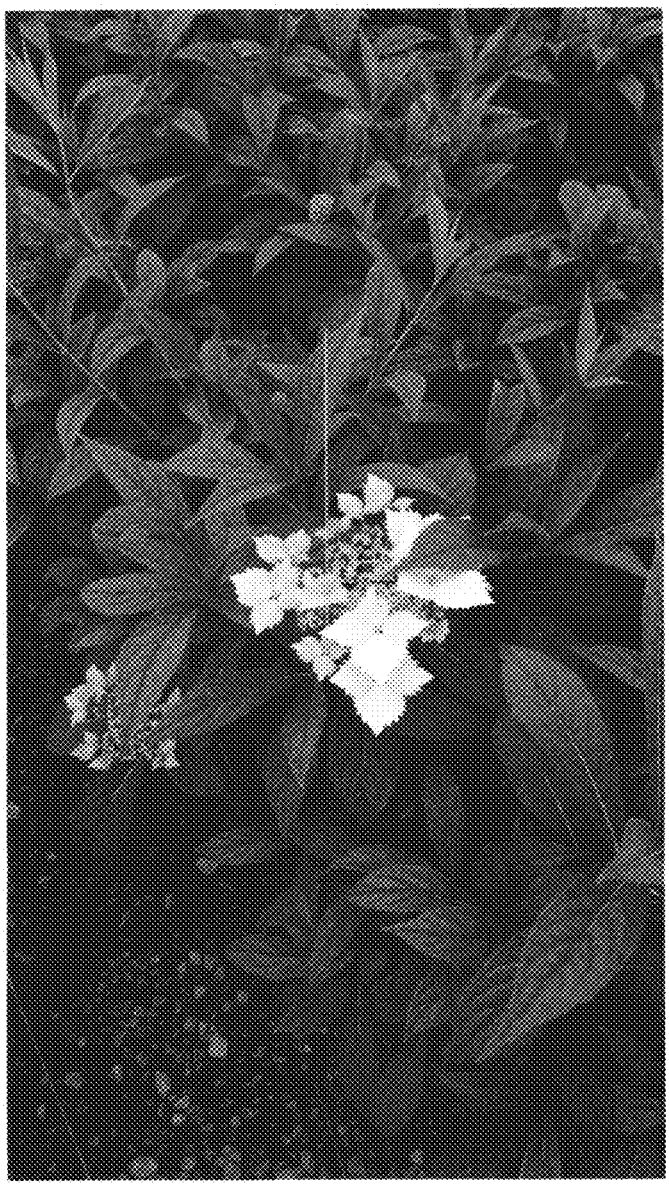

Latin name of the genus and species: *Hydrangea macrophylla* x *angustipetala.*

Variety denomination: 'TMHY18-1'.

BACKGROUND OF THE INVENTION

The new cultivar is a product of a planned breeding program conducted by the inventor, at a research nursery in Suffolk, UK. The objective of the breeding program was to produce new, more floriferous *Hydrangea* varieties with large flowers and upright habits. The crossing resulting in the new variety was made during the Summer of 2014.

The seed parent is the variety *Hydrangea maacrophylla* Lilacina', unpatented. The pollen parent is the variety *Hydrangea angustipetala* 'Golden Crane', unpatented.

The new variety was found and selected by the inventor in the Summer of 2017 at the same nursery in Suffolk, UK.

Asexual reproduction of the new cultivar 'TMHY18-1' was first performed during 2018 at the research nursery in Suffolk, UK, by softwood cuttings. Through subsequent propagation, multiple additional generations have been reproduced, having shown that the unique features of this cultivar are stable and reproduced true to type.

SUMMARY OF THE INVENTION

The cultivar 'TMHY18-1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TMHY18-1.' These characteristics in combination distinguish 'TMHY18-1' as a new and distinct *Hydrangea* cultivar:

1. Lace-cap inflorescences.
2. Sterile flowers composed of large serrated pure white sepals that fade to pink with age.
3. Remontant.
4. Upright, controlled plant habit.
5. Flowers occurring on both terminal and axillar nodes.
6. Honey scented flowers.

PARENT COMPARISONS

Plants of 'TMHY18-1' are similar to plants of the seed parent in most horticultural characteristics, however, plants of 'TMHY18-1' differ in the following:

1. 'Lilacina' has far less serration to the sepals
2. Flowers of 'Lilacina' are unscented
3. The new variety reflowers more abundantly than 'Lilacina.
4. 'Lilacina' flowers only on the terminal bud, the new variety also flowers laterally.
5. 'Lilacina' is far more vigorous and less controlled in growth than the new variety.

Plants of 'TMHY18-1' are similar to plants of the pollen parent in most horticultural characteristics, however, plants of 'TMHY18-1' differ in the following:

1. 'Golden Crane' is more scented than the new variety.
2. 'Golden Crane' has fewer sepals (5 or 6) whereas the new variety has 7 or more.
3. Sepals of 'Golden Crane' will stay pure white; sepals of the new variety turn pink with age.
4. 'Golden Crane' flowers only on the terminal bud, the new variety also flowers laterally.
5. The foliage on 'Golden Crane' is narrower than foliage of the new variety.

COMMERCIAL COMPARISON

Plants of the new cultivar *Hydrangea* 'TMHY18-1' can be compared to the commercial variety *Hydrangea* 'Runaway Bride', patent status unknown. These varieties are similar in most horticultural characteristics; however, 'TMHY18-1' differs in the following:

1. 'TMHY18-1' has a honey scented flower; flowers of this comparator are not fragrant.
2. 'TMHY18-1' has larger sepals with more pronounced serration than this comparator.
3. Plant habit of the new variety is more upright and firm; plant habit of this comparator tends to be more prostrate and lax.

Plants of the new cultivar *Hydrangea* 'TMHY18-1' can be compared to the commercial variety *Hydrangea* 'French Bolero', U.S. Plant Pat. No. 32,055. Plants of 'TMHY18-1' are similar to plants of 'French Bolero' in most horticultural characteristics, however, plants of 'TMHY18-1' differ in the following:

1. 'TMHY18-1' produces white flowers; 'French Bolero' has pink or blue flowers, depending on the soil pH.
2. 'TMHY18-1' has a honey scented flower; flowers of this comparator are not fragrant.
3. 'TMHY18-1' has larger sepals with more pronounced serration than those of 'French Bolero'.
4. Plant habit of the new variety is more upright and firm; plant habit of this comparator tends to be more prostrate and lax.

BRIEF DESCRIPTION OF THE PHOTOGRAPHS

The accompanying photograph in FIG. 1 illustrates in full color a typical flowering plant of 'TMHY18- 1' grown outdoors in Suffolk, UK. Age of the plant photographed is approximately 1 year.

Figure 2:
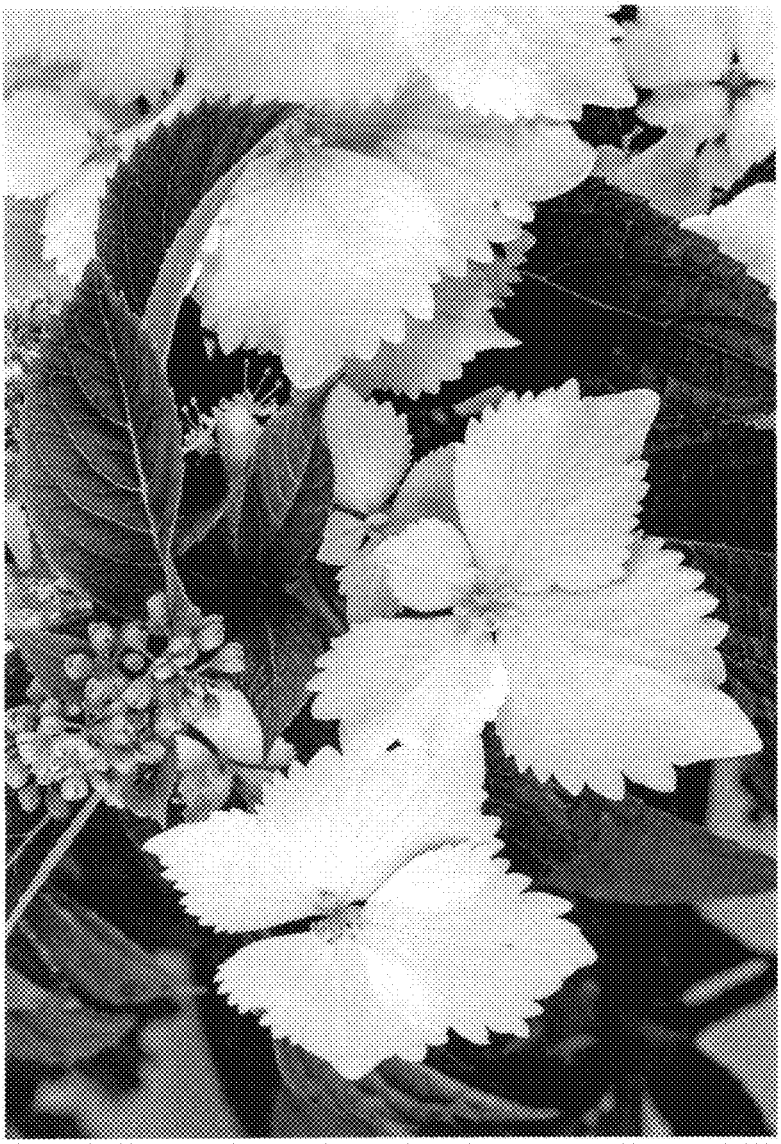

FIG. 2 illustrates a close up of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'TMHY18-1' plants grown outdoors in Camarillo, Calif. The plants were about 2 to 3 years old. Temperatures ranged from 10° C. to 20° C. at night to 15° C. to 27° C. during the day. No artificial light, photoperiodic treatments were given to the plants. Measurements and numerical values represent averages of typical plant types.

Botanical classification: *Hydrangea macrophylla* x *angustipetala* 'TMHY18-1'.

PROPAGATION

Typical method: Softwood cuttings.

Time to initiate roots: Approximately 16 to 28 days at approximately 22 to 27° C.

Time to produce rooted cutting: 30 days during the Summer.

Roots: Medium to thick, moderately free branching, fibrous and fleshy, moderately dense. White in color, not accurately measured with R.H.S. chart.

PLANT

Growth habit: Upwards and outwards. Remontant flowering perennial shrub.

Shape: Rounded.

Height: 45 cm.

Plant spread: 48 cm.

Pot size of plant described: 3-gallon container.

Age of plant described: Approximately 2.5 years.

Branching characteristics: Moderately free branching.

Length of lateral branches: Approximately 20 to 28 cm.

Number of lateral branches: Approximately 18 to 20.

Diameter of lateral branches: Approximately 7 mm.

Pinching required: Yes to encourage branching.

Lateral branch shape: Round.

Lateral branch strength: Very strong.

Lateral branch color: Approximately RHS Greyed-Purple 187A striated N187D.

Lenticels: Not observed.

FOLIAGE

Leaf :

*Arrangement*.—Opposite.

*Compound or single*.—Single.

*Average length*.—Approximately 7 cm.

*Average width*.—Approximately 5 cm.

*Shape of blade*.—Ovate.

*Apex*.—Acute.

*Base*.—Broad taper.

*Attachment*.—Sessile.

*Margin*.—Finely serrate.

*Texture of top surface*.—Glabrous.

*Texture of bottom surface*.—Glabrous.

*Leaf internode length*.—Approximately 3 to 4 cm.

*Color*.—Young foliage upper side: Near R.H.S. Green 139A. Young foliage under side: Near R.H.S. Green 137A Mature foliage upper side: Near R.H.S. Green 139A. Mature foliage under side: Near R.H.S. Green 137B.

*Venation*.—Type: Pinnate. Venation color upper side: Near R.H.S. Yellow-Green 145A. Venation color under side: Near R.H.S. Yellow-Green 145B.

INFLORESCENCE

Natural flowering season: Flowering begins mid-Spring, continues throughout Summer with new inflorescences forming.

*Arrangement*.—Irregular lacecap, occurring both terminally and laterally. Mainly sterile flowers in irregular corymb, with flowers occurring within stem as well as terminally. Fertile flowers rarely present and do not open.

*Corymb height*.—Terminally: Approximately 5 cm. Laterally: Approximately 5 cm.

*Corymb width*.—Terminally: Approximately 10 cm. Laterally: Approximately 5 to 10 cm.

*Quantity of flowers per inflorescence*.—Fertile flowers, approximately 0 to 10, not developing. Sterile Flowers, approximately 1 to 6.

*Flower longevity on plant*.—Fertile flowers: Approximately 5 days, drying, then falling off. Sterile flowers: Approximately 35 days. Persistent.

*Fragrance*.—Honey-scented.

Peduncle:

*Length*.—Approximately 1.8 cm.

*Diameter*.—Approximately 4 mm.

*Strength*.—Strong.

*Texture*.—Glabrous.

*Color*.—Near R.H.S. Yellow-Green 144C.

Fertile flower bud:
*Bud shape*.—Obovate.
*Bud length*.—Approximately 6 mm.
*Bud diameter*.—Approximately 3 mm.
*Bud color*.—Near Yellow-Green 144C.
Fertile flower: Does not develop from bud, flower aborts.
Sterile flower bud:
*Bud shape*.—Obovate.
*Bud length*.—Approximately 9 mm.
*Bud diameter*.—Approximately 7 mm.
*Bud color*.—Near Yellow-Green 145B.
Sterile flower:
*Facing direction*.—Upright.
*Diameter of entire flower*.—Average range 2.5 cm to 6.5 cm.
*Depth of flower*.—Approximately 1.5 cm.
Sepals:
*Quantity*.—4.
*Sepal arrangement*.—Cruciform.
*Length of sepal*.—Average range 1.5 cm to 3.5 cm.
*Width of sepal*.—Approximately 1 cm to 2.5 cm.
*Apex*.—Acute.
*Shape of sepal*.—Rounded diamond.
*Sepal margin*.—Deeply serrate.
*Sepal number*.—Average 4.
*Sepals fused*.—No.
*Sepal appearance*.—Matte all surfaces.
*Sepal texture*.—Smooth all surfaces.
Color:
*Upper surface at first opening*.—Near White N155D, very slightly flushed Yellow-Green 145C.
*Upper surface at maturity*.—Near White N155D.
*Upper surface with age*.—Near RHS Red 49D.
*Under surface at first opening*.—Near White N155D, very slightly flushed Yellow-Green 145C.
*Under surface at maturity*.—White N155D.
*Under surface with age*.—Near RHS Red 49D.
Sepaloids: No.
Sterile flower pedicel:
*Length*.—Approximately 1 to 2.5 cm.
*Diameter*.—Approximately 3 mm.
*Strength*.—Moderate.
*Texture*.—Glabrous.
*Color*.—Near Yellow-Green 145B.

REPRODUCTIVE ORGANS

Sterile flower:
Stamens:
*Number*.—5 to 10.
*Filament color*.—RHS White 155A.
*Filament length*.—1 mm.
Anthers:
*Length*.—About 1 mm.
*Shape*.—Rounded, globular.
*Color*.—RHS Yellow-White 158A.
*Pollen*.—Not observed.
Pistil:
*Number*.—1.
*Length*.—2 mm.
Stigma:
*Shape*.—3-lobed.
*Color*.—RHS White 155A.
*Style length*.—1 mm.
*Style color*.—RHS White 155A.

OTHER CHARACTERISTICS

Disease resistance: Neither resistance nor susceptibility to the normal diseases and pests of *Hydrangea* has been observed.
Drought tolerance and cold tolerance: USDA Zones 7 through 10.
Fruit/seed production: Not observed to date.

What is claimed is:

1. A new and distinct cultivar of *Hydrangea* plant named 'TMHY18-1' as herein illustrated and described.

* * * * *